US006252096B1

(12) United States Patent
Spielmann et al.

(10) Patent No.: US 6,252,096 B1
(45) Date of Patent: Jun. 26, 2001

(54) TETRAFLUOROAZIDOANILINE AND METHOD OF MAKING AND USING THE SAME

(75) Inventors: Hans Peter Spielmann, Lexington; Kareem Abdel Hassan Chehade, Lex, both of KY (US)

(73) Assignee: University of Kentucky Research Foundation, Lexington, KY (US)

(*) Notice: Subject to any disclaimer, the term of this patent is extended or adjusted under 35 U.S.C. 154(b) by 0 days.

(21) Appl. No.: 09/525,753

(22) Filed: Mar. 14, 2000

(51) Int. Cl.[7] .................................................. C07C 247/10
(52) U.S. Cl. ................................................. 552/8; 548/303
(58) Field of Search ............................... 552/8; 536/22.1; 548/303

(56) References Cited

U.S. PATENT DOCUMENTS 4,898,951 * 2/1990 Symons .
5,854,409 * 12/1998 Westling et al. .

OTHER PUBLICATIONS

J. Michalak et al., J. Physical Chemistry, 1996: 100(33), 14028–14035.*
"The Merck Index: An Encyclopedia of Chemicals, Drugs, and Biologicals" by Windholz et al., p. 594. (1983).
"Nitrosations Anhydrous Trifluoroacetic Acid Media: A Modification for Insoluble or Deactivated Amine and Amide Precursors", by Kanakarajan et al., *Communications*, pp. 566–568 (Jul. 1998).
"Perfluoroaromatic Diamines" by Holland et al., *Chemistry and Industry*, pp. 1376–1377 (Jul. 31, 1965).
"Polyfluorarenes. Part X. Polyfluoroaromatic Azo–compounds" by Birchall et al., *J. Chem. Sco.*, pp. 449–455 (1970).
"Aromatic Polyfluoro–compounds. Part VII. The Reaction of Pentafluoronitrobenzene with Ammonia" by Brooke et al., *J. Chem. Soc.*, pp. 802–807 (1961).
"Nucleophilic Displacement in Polyhalogenoaromatic Compounds. Part 9. Kinetics of Azidodefluorination and Methoxydefluorination of Some Polyfluorobenzonitriles" by Bolton et al., *J. Chem. Soc.*, J.C.S. Perkin II, pp. 1288–1292 (1978).
"4–azido–2–iodo–3,5,6–trifluorophenylcarbonyl Derivatives. A New Class of Functionalized and Iodinated Perfluorophenyl Azide Photolabels" by Cai et al., *Tetrahedron Letters*, vol. 30, No. 40, pp. 5409–5412 (1989).
"Polyfluorinated Aryl Azides as Photoaffinity Labelling Reagents; The Room Temperature CH Insertion Reactions of Singlet Pentaafluorrophenyl Nitrene with Alkanes" by Young et al., *Tetrahedron Letters*, vol. 30, No. 17, pp. 2199–2202 (1989).
"Photoaffinity Labeling", by Schuster et al., Photochemistry and Photobiology, vol. 49, No. 6, pp. 785–804 (1989).
"Photochemistry of Fluorinated Aryl Azides in Toluene Solution and in Frozen Polycrystals" by Leyva et al., *J. Org. Chem.*, vol. 54, pp. 5938–5945 (1989).
"Descriptive Photochemistry of Polyflyourinated Azide Derivatives of Methyl Benzoate" by Soundararajan et al., J.Org. Chem., vol. 55, No. 7, pp. 2034–2044 (1990).
"Chemistry and Kinetics of Singlet (Pentafluorohpenyl)nitrene" by Poe et al., *American Chemical Society*, vol. 114, No. 13, pp. 5054–5067 (1992).
"Photochemistry of Phenyl Azide: The Role of Singlet and Triplet Phenylnitrene as Transient Intermediates" by Leyva et al., *J. Am. Chem. Soc.*, vol. 108, No. 13, pp. 3783–3790 (1986).
"Synthesis of a Tetrafluoro–Substituted Aryl Azide and Its Protio Analogue as Photoaffinity Labeling Reagents for the Estrogen Receptor" by Pinney et al., *J. Org. Chem.*, vol. 56, No. 9, pp. 3125–3133 (1991).
"Competitive Single–Singlet Energy Transfer and Electron Transfer Activation of Aryl Azides: Application to Photo–Cross–Linking Experiments" by Shields et al., *J. Org. Chem.*, vol. 53, No. 15, pp. 3501–3507 (1988).
"New Reagents for Photoaffinity Labeling: Synthesis and Photolysis of Functionalized Perfluorophenyl Azides" by Keana et al., *J. Org. Chem.*, vol. 55, No. 11, pp. 3640–3647 (1990).
"Functionalized Perfluorophenyl Azides: New Reagents for Photoaffinity Labeling" by Keana et al., *Journal of Fluorine Chemistry*, vol. 43, pp. 151–154 (1989).
"Azides: Their Preparation and Synthetic Uses" by Scriven et al., *Chemical Reviews*, vol. 88, No. 2, pp. 297–368 (1988).

* cited by examiner

Primary Examiner—Johann Richter
Assistant Examiner—Sikarl A. Witherspoon
(74) Attorney, Agent, or Firm—McDermott, Will & Emery

(57) ABSTRACT

The invention is directed to a novel compounds comprising 4-azidotetrafluoroaniline and the alkyl, acyl and sulfonamide derivatives thereof and to methods of making and using the same. The novel compounds are useful as a photoaffinity probe to study protein structure and function. Two methods for preparing 4-azidotetrafluoroaniline are disclosed, each employing a stable carbamate intermediate from which the 4-azidotetrafluoroaniline is derived.

6 Claims, No Drawings

TETRAFLUOROAZIDOANILINE AND METHOD OF MAKING AND USING THE SAME

FIELD OF INVENTION

The present invention relates to a fluorinated aryl azide and the method of making and using the same as an photoaffinity probe and photoreactive group. In particular, the fluorinated aryl azide is 4-azidotetrafluoroaniline or an alkyl, acyl or sulfonamide derivative thereof.

BACKGROUND OF THE INVENTION

Perfluorophenyl azides have been used extensively in the biochemistry and molecular biology fields as photoaffinity probes to study protein structure and function. In addition, aryl azides have been used in optical lithography as photoresists. A photoaffinity probe is a labeling reagent that has a photoactive moiety such as an azido or diazo group that forms a stable covalent bond with a targeted protein by CH insertion.

For example, an azide labeling reagent can be attached to an active site of an enzyme molecule. When the labeled enzyme is exposed to ultraviolet light, there is a loss of nitrogen and the formation of a highly reactive intermediate, a singlet nitrene, which reacts rapidly with a nearby protein molecule such that the protein forms a covalent bond with the enzyme.

Para-substituted pentafluorophenyl azides are among the most popular labeling agents used as photoaffinity probes. Their popularity stems from the fact that non-fluorinated arylazides do not form the highly reactive singlet nitrene intermediate upon photoactivation, rather they form an electrophilic dehydroazepine intermediate with a very different and undesirable reactivity. A variety of these azides have been synthesized in accordance with the following reaction:

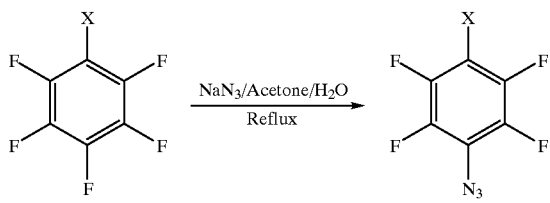

wherein X is an electron withdrawing group such as CN, $CONH_2$, CHO, $CO_2CH_3$, $COCH_3$ and $NO_2$ (Keana et al., J. Org. Chem., Vol. 55, No. 11, pp. 3640–3647 (1990)). All of the prior art perfluorophenyl azide photoaffinity labeling agents have electron-withdrawing groups para to the azido functionality. There is a need for a photoaffinity labeling agent having a chemically reactive electron donating group para to the azido functionality. There is also a need for photoreactive crosslinking agents which are hetero-bifunctional having a chemically reactive electron donating group para to the azido functionality.

Photoreactive crosslinking reagents are important tools for determining the proximity of two sites on a molecule or between two molecules. These probes can be employed to define relationships between two reactive groups on a protein molecule, on a ligand and its receptor, or on separate biomolecules within an assembly. In the latter case, photoreactive crosslinking reagents can potentially reveal interactions among proteins, nucleic acids, and membranes in live cells. The general scheme for defining spatial relationships usually involves photoreactive crosslinking reagents that contain a chemically reactive group as well as a photoreactive group. These crosslinkers are first chemically reacted with one molecule, for example a receptor ligand, and then this modified molecule is coupled to a second molecule, for example the ligand's receptor, using UV illumination. Depending on the reactive properties of the chemical and photoreactive groups, these crosslinkers can be used to couple like or unlike functional groups. Fluorinated aryl azides are useful in these processes because they generate nitrenes, thereby producing more C—H insertion products than the simple aryl azides.

Simple aryl azides may be initially photolyzed to electron-deficient aryl nitrenes that rapidly ring-expand to form dehydroazepines thereby producing molecules that tend to react with nucleophiles rather than form C—H insertion products. Photolysis products of the fluorinated aryl azides are clearly aryl nitrenes and undergo characteristic nitrene reactions such as C—H bond insertion with high efficiency.

A photocrosslinking agent known in the art is 4-azido-2,3,5,6-tetrafluorobenzyl amine. This benzylic amine has a pKa of approximately 9. The crosslinking reagents of the present invention have an anilino nitrogen, and not a benzylic amine, and have a pKa closer to -1 pKa units. In addition, the nitrogen in the prior art crosslinking agent is one carbon further away from the amino functionality than in the 4-tetrafluoroaniline azide. Because hetero-bifunctional crosslinking probes have demonstrated utility for determining the proximity of two sites on a molecule or between two different molecules, the 4-tetrafluoroaniline azide molecule allows the generation of probes that are an atom shorter than current probes, thus allowing shorter distances to be probed.

SUMMARY OF THE INVENTION

The object of this invention is to provide new photoaffinity labeling agents having a chemically reactive electron-donating amino group para to the azido functionality. Another object of the invention is to provide a photoaffinity labeling agent which will extend the range of existing hetero-bifunctional crosslinking reagents. A further object of the invention is to provide a compound, 4-azidotetrafluoroaniline, and its alkyl, acyl and sulfonamide derivatives, having a chemically reactive electron-donating amino group para to the azido functionality. A still further object of the invention is to provide a method of making 4-azidotetrafluoroaniline, or its alkyl, acyl or sulfonamide derivative from a stable carbamate intermediate. Still another object of the invention is to provide for a method of using 4-azidotetrafluoroaniline, or its alkyl, acyl or sulfonamide derivative as a photoaffinity labeling agent. The other objects and characteristics of the present invention will become apparent from the further disclosure of the invention.

DETAILED DESCRIPTION OF THE INVENTION

The present invention is directed to a novel 4-tetrafluoroaniline azide and to the mono- and di-substituted alkyl, acyl, or sulfonamide derivatives thereof, including mono-alkyl-mono-sulfonyl derivatives, and the method of making and using the same as a photo affinity probe. In particular, the compounds of the invention have the following formula:

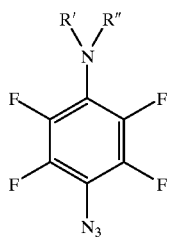

wherein R' and R" are independently hydrogen, $C_1$–$C_8$ alkyl, $C_1$–$C_8$ allylic, unsubstituted benzyl, or benzyl substituted with up to five substituents selected from the group consisting of $NO_2$, $N_3$, $NH_2$, $NHR'''$, $N(R''')_2$, $N(R''')_3^+$, halogen, and $C_1$–$C_8$ alkyl where R''' is hydrogen, $C_1$–$C_8$ alkyl, $C_1$–$C_8$ allylic, or an unsubstituted benzyl. The most preferred compound is the unsubstituted compound, 4-azidotetrafluoroaniline (I) having the following formula:

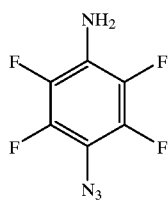

(I)

The most preferred derivatives of 4-azidotetrafluoroaniline are N-iodo-actamido-4-tetrafluoroaniline azide and 1-(4-azido-tetrafluoroaniline)-dansylsulfonamide.

When 4-azidotetrafluoroaniline (I) or its alkyl, acyl or sulfonamide derivative is irradiated with ultraviolet light in the presence of cyclohexane in accordance with the following reaction scheme, three primary products are formed: 1,4-diaminotetrafluorobenzene (II), cyclohexylaminotetrafluorobenzene (III) and azotetrafluorobenzene (IV). The reaction is exemplified below with respect to 4-azidotetrafluoroaniline.

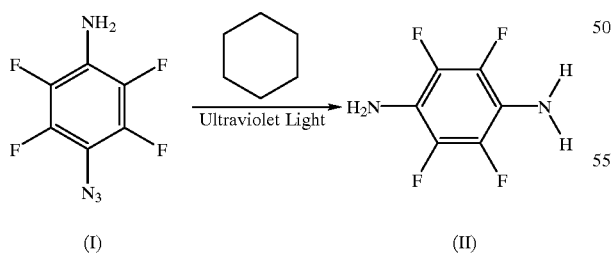

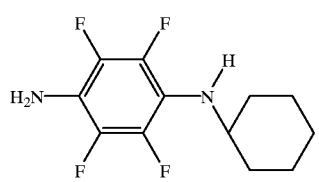

(III)

(IV)

The formation of C—H insertion product (III) indicates that 4-azidotetrafluoroaniline forms a singlet nitrene upon photolysis.

The novel 4-azidotetrafluoroaniline compound is made by forming a stable carbamate intermediate and then converting the carbamate to 4-azidotetrafluoroaniline. Two embodiments are disclosed.

In the first embodiment, a stable carbamate is formed via a modified Curtius rearrangement by transforming 4-azidotetrafluorobenzoic acid into an intermediate acid chloride, converting the acid chloride into an acyl azide, and further converting the acyl azide into an isocyanate by thermal rearrangement. A stable carbamate is formed by reacting the isocyanate with an alcohol. The carbamate includes an acid labile group which is derived from the alcohol. The carbamate is then converted to 4-azidotetrafluoroaniline by removal of the acid labile group. The reaction scheme for the first embodiment is illustrated as follows:

Reaction Scheme I

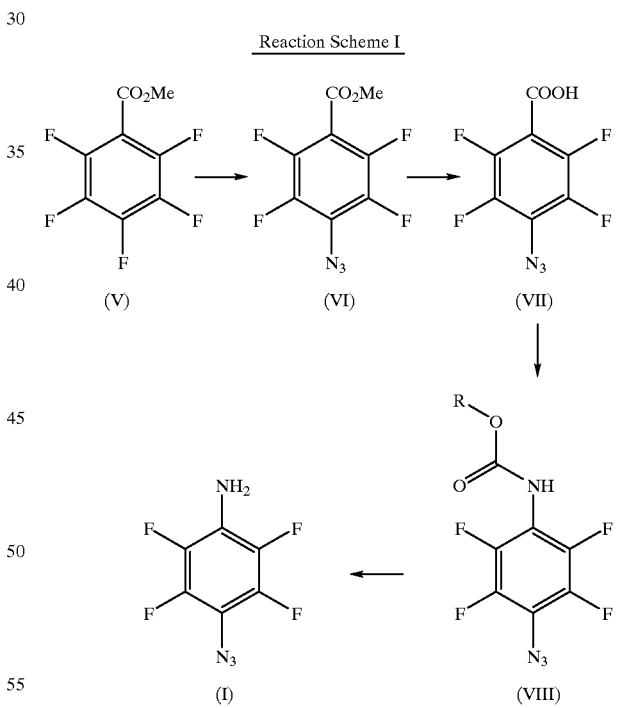

wherein R is acid labile group such as $(CH_3)_3C-$ or $(CH_3)_3SiCH_2CH_2-$. In particular, methylpentafluorobenzoate (V) is converted to 4-azidomethyltetrafluorobenzoate (VI) by the nucleophilic substitution with $NaN_3$ in the presence of water and acetone. The 4-azidomethyltetrafluorobenzoate is subjected to hydrolysis with NaOH in aqueous methanol to give 4-azidotetrafluorobenzoic acid (VII). Compound (VII) is converted to an intermediate carbamate (VIII) by converting it to an its acid chloride, reacting the acid chloride with NaN₃ to form an azide derivative, transforming the azide derivative into the isocyanate by heating the azide and then reacting the isocyanate with an alcohol capable of forming an acid labile group. The preferred alcohol is t-butanol or 2-trimethylsilylethanol. The carbamate (VIII) is treated to remove the acid labile group to form 4-azidotetrafluoroaniline (I). If the acid labile groups is (CH₃)₃C—, the carbamate (VIII) is treated with a solution of HCl in acetic acid. If the acid labile group is (CH₃)₃SiCH₂CH₂—, trifluoroacetic acid is used to form 4-azidotetrafluoroaniline (I).

The second embodiment of the invention is a five step process wherein a stable carbamate having a N-9-fluorenylmethoxycarbonyl group which functions as a base labile group is formed. The carbamate, 4-amino-(N-9-fluorenylmethoxycarbonyl)-tetrafluoroaniline, is formed by reacting N-9 fluorenyl-methoxycarbonyl chloride with p-aminotetrafluoroaniline. The N-9-fluorenylmethoxycarbonyl group functions as a protective group. The carbamate is converted to an azide which is then converted to 4-azidotetrafluoroaniline by removal of the base labile group. The reaction scheme for the second embodiment is illustrated below:

In particular, pentafluoronitrobenzene (IX) is converted to 4-azidotetrafluoro-nitrobenzene (X) by nucleophilic substitution with NaN₃ in the presence of water and acetone. Compound (X) is reduced with Sn and HCl in ethanol to form 1,4-diaminotetrafluorobenzene (XI) which is converted to fluroenylmethoxycarbonyl carbamate (XII) by reacting it with N-9-fluroenylmethoxycarbonyl chloride in the presence of pyridine and ethyl acetate. The fluroenylmethoxycarbonyl group on the amino group is a base labile group and functions as a protective group for the amine. Compound IX is reacted with NaNO₂, followed by NaN₃, to form 4-(3-nitro-N-9-fluorenylmethoxycarbonyl) tetrafluoroaniline azide (XIII). The base labile group is removed by using piperidine to form 4-azidotetrafluoroaniline (I).

The formation of derivatives of 4-tetrafluoroaniline azide allows for the formation of a bifunctional cross linking agent. As already noted, bifunctional photoreactive cross-linking reagents are important tools for determining the proximity of two sites on a molecule or between two molecules.

The aniline nitrogen may be alkylated by reductive amination utilizing NaBH(OAc)₃ with any aldehyde function

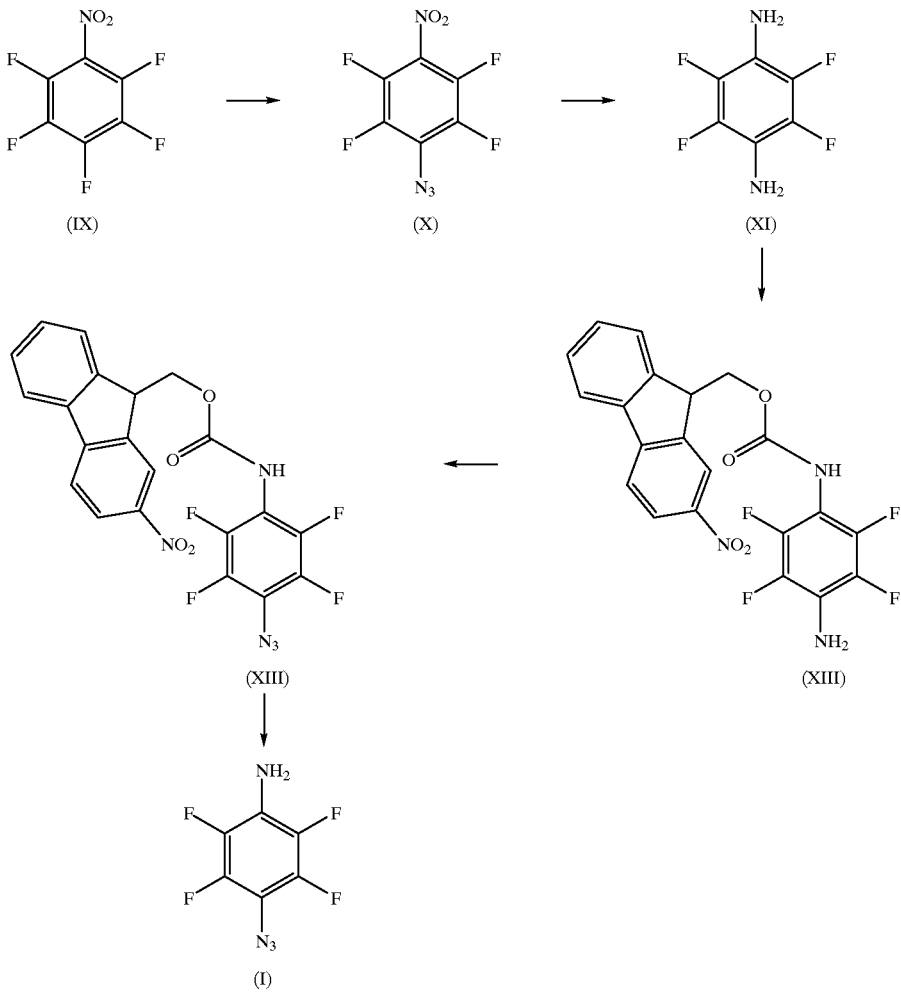

Reaction Scheme II and a Lewis acid catalyst such as $TiCl_4$. The $NaBH(OAc)_3$ is a mild enough reducing agent such that the azide function is not damaged.

The aniline nitrogen may be acylated by a chloroacetyl chloride and then converted to an iodoacetyl via the Finkelstein reaction to form N-iodo-acetamido-4-tetrafluoroaniline azide. This molecule includes an iodoacetamido functionality which is reactive with a wide range of nucleophilic moieties. Specific examples include the thio of cysteine residues of proteins and amino groups of lysine residues on proteins. The reaction of the iodoacetamido group with one of these nucleophiles forms a covalent bond between the acetamido-4-tetrafluoroaniline azide and the molecule bearing the nucleophile. The covalent bond forming reaction does not interfere with the 4-tetrafluoroaniline azide portion of the molecule. The new molecule provides heterobifunctional crosslinking agent properties such that acetamide-4-azido-tetrafluoroaniline function can be photoactivated to form either intra-molecular or inter-molecular crosslinks through the nitrene intermediate.

When 4-tetrafluoroaniline azide is reacted with danzyl chloride or sulfonyl chloride, the corresponding sulfonamide derivative is formed. The 1-(4-azido-tetrafluoroaniline)-dansylsulfonamide derivative is a fluorescent photoaffinity probe that allows the fluorescent labeling of non-polar residues and surfaces with the dansyl moiety. It is activated to form a singlet nitrene upon photolyis with either shortwave or longwave length UV light. The dansylsulfonamide derivative probe allows for spatially defined fluorescent labeling of substrates because the formation of a covalent bond is dependent on photoactiviation. This has the utility in generating specific patterns of fluorescence by microphotolithography on surfaces.

Examples 1 and 2 below set forth in the detail the two embodiments. Example 1 is Reaction Scheme I while Example 2 is Reaction Scheme II. Because aryl azides are light sensitive, all reactions and flash chromatography procedures were conducted under diminished light. Further, all of the reactions described below were conducted under dry argon and stirred magnetically. Reaction temperatures referred to in Examples 1 and 2 are external bath temperatures. Example 3 below sets forth in detailed steps for forming the acyl and sulfonamide derivatives.

EXAMPLE 1

Preparation of 4-Azidotetrafluoromethylbenzoate

Into a 250 ml round bottom flask equipped with reflux condenser was added 80 ml acetone, 31 ml water, 3.09 g (47.6 mmol) of sodium azide, and 10.0 g (44.2 mmol) of tetrafluoromethylbenzoate with stirring to form a mixture which was then refluxed for 16 hours. The mixture was cooled, diluted with 100 ml water, poured into 200 ml $CHCl_3$, and extracted (3×) with $CHCl_3$. The combined organic extracts were then washed with water, dried with $Na_2SO_4$ and evaporated to yield 10.60 g (96% yield) of a colorless liquid which solidified into a colorless solid consisting of 4-azidotetrafluoromethylbenzoate having a melting point of 54–55° C.

Preparation of 4-Azidotetrafluorobenzoic Acid

A solution was prepared by mixing 10.60 g of 4-azidotetrafluoromethylbenzoate with 180 ml MeOH and 18 ml water. To this solution, 15 ml of 20% aqueous NaOH was added. The resultant solution was stirred overnight at 25° C. The stirred solution was placed in an ice bath and acidified by adding 2N HCl to the solution reduce the pH of the solution to less than 1. The resultant organic material extracted with $CHCl_3$ (3×, 150 ml). The organic extracts were combined, washed once with water, and then dried with $MgSO_4$. The solution was filtered and concentrated to leave 9.83 g (98%) of 4-azidotetrafluorobenzoic acid as a colorless solid. Sublimation (80° C., 0.5 mm Hg) gave the analytical sample of 4-azidotetrafluorobenzoic acid as colorless needles having a melting point of 140–141° C.

General Procedure for the Carbamate Synthesis and Formation of 4-Azidotetrafluoroaniline 2.00 g (8.51 mmol) of 4-azidotetrafluorobenzoic acid was dissolved in 30 ml of ethyl ether followed by the addition of 1.88 g (9.02 mmol) $PCl_5$. The mixture was stirred for 1 hour at room temperature. The solvent was removed in vacuo leaving a yellow oil which was further dried for 1 hour at 25° C. under vacuum to form an acid chloride of 4-azidotetrafluorobenzoic acid. The acid chloride was dissolved in 45 ml of dry acetone, and the resulting solution was added dropwise to a rapidly stirred solution of 2.03 g (31.2 mmol) sodium azide in 6.5 ml of water at 0° C. After 15 minutes, 60 ml hexane and 60 ml water were added. The hexane layer was removed and the aqueous layer was extracted with hexane again. The hexane layer and the extracted organic material extracted from the aqueous layer are dried with $MgSO_4$, filtered and concentrated to form an acyl azide. The acyl azide was then dissolved in 20 ml anhydrous benzene and heated at 70° C. After heating at 70° C. for one hour, either 5 ml (52.3 mmol) of anhydrous tert-butanol or 2.5 ml (17.4 mmol) of 2-trimethylsilylethanol was added. The solution was stirred at 70° C. for an additional six hours to form the carblamate. The red-violet reaction mixture was concentrated, loaded into a silica column, and purified by flash chromatography (5% EtOAc in hexane).

Tert-butanol formed 2.29 g of a carbamate identified as 4-(N-tert-butyloxycarbonyl)tetrafluoroazide. Sublimation (70° C., 0.5 mm Hg) following by crystallization from hexane provided the analytical sample of 4-(N-tert-butyloxycarbonyl)tetrafluoroazide as colorless prismatic needles having a melting point of 80° C. In a 50 ml pear-shaped flask, 1.31 g (4.28 mmol) 4-(N-tert-butoxycarbonyl)-tetrafluoroazide was dissolved in 5 ml methyl dichloride at 0° C. To the solution, 15 ml of a 1 M HCl solution in acetic acid was added. The solution was stirred at 0° C. for two hours and then stirred at room temperature for 12 hours. 20 ml of water was added to the mixture and the mixture was transferred to a separatory funnel containing 150 ml hexane/ethyl ether (1:1 v/v) and 20 ml water. The aqueous layer was discarded and the organics were then washed with 5% $NaHCO_3$, and water and then dried with $MgSO_4$, filtered over a short pad of silica gel, and concentrated to yield 0.73 g of 4-azidotetrafluoroaniline.

2-Trimethylsilylethanol formed 2.74 g of a carbamate identified as 4-(N-2-trimethylsilylethoxycarbonyl) tetrafluoroazide. 1.50 g (4.28 mmol) of the carbamate was dissolved in 25 ml of methyl dichloride at 0° C. To the resultant solution was added 2.5 ml trifluoroacetic acid. The solution was stirred at 0° C. for three hours and then for 12 hours at room temperature. The reaction mixture was slowly quenched by the addition of a saturated $NaHCO_3$ solution. The reaction mixture was transferred to a separatory funnel containing 100 ml of ether and 20 ml of water and shaken. The aqueous layer was discarded. The organic layer was washed with water, dried with $MgSO_4$, filtered through a pad of silica gel, and concentrated to yield 0.76 g of 4-azidotetrafluoroaniline.

EXAMPLE 2

Preparation of Tetrafluorophenylenediamine

Commercially available pentafluoronitrobenzene was converted into 4-azidotetrafluoronitrobenzene by nucleophic aromatic substitution with $NaN_3$ by methods well known in the art. Into a 500 ml round bottom flask equipped with reflux condenser was added, with stirring, 25.0 g (0.12 mol) of pentafluoronitrobenzene, 200 ml of acetone, 75 ml of water, and 8.15 g (0.13 mol) of sodium azide. The resultant solution immediately intensified in color and was brought to reflux for 12 hours. The solution was cooled and diluted with 50 ml of water. Acetone was removed from the solution under reduced pressure. The remaining mixture was then poured into 200 ml of $CH_2Cl_2$, and organic residues extracted (3×) with $CH_2Cl_2$. The extracted organic residues were then washed with water and brine, and then dried with $MgSO_4$. The residues were then filtered through a short pad of silica gel that was rinsed with 200 ml $CH_2Cl_2$. The $CH_2Cl_2$ was evaporated under reduced pressure to yield a yellow-orange oil of 4-azidotetrafluoronitrobenzene which required no further purification.

Into a 1000 ml three neck round bottom flask equipped with reflux condenser was added 200 ml of 95% EtOH and 60 g (0.51 mol) of powdered tin (325 mesh) with stirring to form a heterogeneous mixture. To this mixture, 26.41 g (0.12 mole) of 4-azidotetrafluoronitrobenzene dissolved in 50 ml 95% EtOH was slowly added followed by the dropwise addition of 140 ml of concentrated HCl over 30 minutes. The mixture was refluxed for 4 hours, cooled to room temperature, and placed into an ice-bath. The mixture was made basic by the slow addition of 160 g NaOH dissolved in 250 ml of water. The mixture was warmed to room temperature and 100 g of NaCl was added. The mixture was poured into a 2 liter separatory funnel containing 600 ml of ether, and organic residues extracted (3×) with ether. The organic residues were washed with water and then with brine, and dried over $MgSO_4$. The remaining residues were filtered and evaporated resulting in the formation of an off-white/pink solid. The solid was purified by sublimation (90° C. per 0.5 mm) to yield 17.88 g of colorless crystals of tetrafluorophenylenediamine having a melting point of 143–145° C. These crystals were stored in a foil-wrapped container under argon at −20° C.

Preparation of the N-9-Fluorenylmethoxycarbonyl Carbamate

Into a 250 ml 3-neck flask equipped with a 50 ml addition funnel was introduced 8.35 g (46.4 mmol) of freshly purified tetrafluorophenylenediamine, 100 ml of dry EtOAc, and 3.75 ml (46.4 mmol) of anhydrous pyridine. After stirring to homogeneity at room temperature, the flask was immersed in an ice bath, and 10.0 g (38.7 mmol) of N-9-fluorenylmethoxycarbonyl chloride dissolved in 35 ml dry EtOAc was added dropwise to the solution over a 30 minute period. The mixture was stirred at 0° C. for 4 hours, and then stored at room temperature overnight. The reaction mixture was poured into a separatory funnel containing 500 ml of EtOAc, and the organic layer was washed with cold 1 N HCl (2×), water and then with brine. The product was dried with $Na_2SO_4$ and concentrated, resulting in the formation of off-white crystals which were subsequently recrystallized from $CHCl_3$/hexane to yield 14.30 g of the carbamate, 4-(N-9-fluorenyl-methoxycarbonyl)tetrafluoroaniline, as fine colorless needles having a melting point of 189° C.

Preparation of 4-(3-Nitro-N-9-Fluorenylmethoxycarbonyl)tetrafluoroazide 6.00 g (14.9 mmol) of 4-(N-9-fluorenylmethoxycarbonyl) tetrafluoroaniline was dissolved in 100 ml of trifluoroacetic acid and stirred at 0° C. for 10 minutes to which 4.12 g (50.3 mmol) of solid $NaNO_2$ was added in portions over 15 minutes. After addition of the $NaNO_2$, stirring was continued for an additional 15 minutes resulting in a red-violet solution to which 3.27 g (50.3 mmol) of solid $NaN_3$ was added over a 10 minute period. The solution was then stirred at 0° C. for 80 minutes. The temperature of the solution was raised to room temperature over 10 minutes. The solution was then poured onto 400 ml of ice-water and stirred. After 5 minutes of stirring, a solid was formed. The solid was filtered, washed with water (2×) and dried in vacuo at 40° C. 6.30 grams of 4-(3-nitro-N-9-fluorenylmethoxycarbonyl) tetrafluoroazide (an off-white solid) having a melting point of 151–152° C. was obtained by recrystallization from a mixture of $CH_2Cl_2$ and pentane.

Preparation of 4-Azidotetrafluoroaniline

Into a 250 ml round bottom flask was added 3.08 g (6.51 mmol) of 4-(2-nitro-N-9-fluorenylmethoxycarbonyl) tetrafluoroazide and 100 ml of ethyl ether. The mixture was placed in an ice bath and 10 ml (0.10 mol) of piperidine was added to the mixture. The resultant solution was stirred at 0° C. for 50 minutes and then at room temperature for 10 minutes. The solution was poured into a one liter separatory funnel containing 200 ml ice-cold 2N HCl and 150 ml ethyl ether. The aqueous layer was discarded and the resultant organic solution was washed with 1N HCl, water, and brine. The solution was dried with $MgSO_4$, filtered, and concentrated to yield a crude orange-brown solid. The solid was purified by sublimation to give 1.25 g of 4-azidotetrafluoroaniline as golden crystals having a melting point of 68–71° C.

EXAMPLE 3

Two derivatives of 4-azidotetrafluoroaniline were prepared, each having utility as a hetero-bifunctional photoaffinity reagent. The derivatives prepared were N-iodoacetamido-4-tetrafluoroanaline azide and 1-(4-azidotetrafluoroaniline)-dansylsulfonamide.

Preparation of N-Iodo-Acetamido-4-Tetrafluoroanaline Azide

A 50 ml round bottom flask was charged with 0.53 g (2.57 mmol) of 4-azidotetrafluoroaniline, 0.50 ml (3.78 mmol) of collidine, and 25 ml of anhydrous EtOAc. After stirring to homogeneity at room temperature, 3.00 ml (37.7 mmol) of chloroacetyl chloride, dissolved in 5 ml dry EtOAc, was added dropwise to the solution over a 30 minute period. The reaction mixture was then stirred at room temperature for 6 hours. The mixture was poured into a separatory funnel containing 150 ml of EtOAc, and the organic layer was washed with water, 1 N HCl, and 5% $NaHCO_3$. The etheral layer was then dried with $MgSO_4$ and concentrated. The residual solid was purified by flash chromatography (10% EtOAc in hexane) to yield 0.57 g of a white solid of 4-(N-chloroacetyl)tetrafluoroazide having a melting point of 109–110° C. This compound is converted to the corresponding iodide, 4-(N-iodoacetyl)tetrafluoroazide, via the Finkelstein reaction. Into a 50 ml round bottom flask was added 0.36 g (1.27 mmol) of 4-(N-chloroacetyl)tetrafluorazide followed by 20 ml dry acetone and 1.91 g (12.7 mmol) of NaI. The solution was stirred at room temperature overnight. The mixture was poured into a separatory funnel containing 150 ml Et$_2$O, washed once with water, and dried with MgSO$_4$. Recrystalization from cyclohexane afforded 0.44 g (93%) of 4-(N-iodoacetyl)tetrafluoroazide (fine colorless needles) having a melting point of 151–153° C. The iodide derivative is attractive because the chemically reactive iodoacetamido group is conjugated to the perfluoroaryl azide which can form a singlet nitrene upon UV irradiation.

Preparation of 1-(4-Azido-Tetrafluoroaniline)-Dansylsulfonamide

To a solution of 0.206 g (1.00 mmol) of 4-azidotetrafluoroaniline in 10 ml of anhydrous THF at –78° C. was added 0.278 g (1.03 mmol) of dansyl chloride immediately followed by 1 ml (1.00 mmol) of lithium bis(trimethylsilyl) amide (1 M solution in THF). The solution was stirred at –78° C. for 2 hours. The solution was slowly warmed to room temperature, and stirred for an additional hour. The solution was concentrated and purified by flash chromatography (15% EtOAc in hexane). Fractions containing dansyl sulfonamide were combined and concentrated affording 0.295 g (67%) of 1-(4-azido-tetrafluoroaniline)-dansylsulfonamide.

While this invention has been described with reference to several preferred embodiments, it is contemplated that various alterations and modifications thereof will become apparent to those skilled in the art upon a reading of the preceding detailed description. It is therefore intended that the following appended claims be interpreted as including all such alterations and modifications as fall within the true spirit and scope of this invention.

What is claimed is:

1. A compound for use as a photoaffinity probe having the following formula:

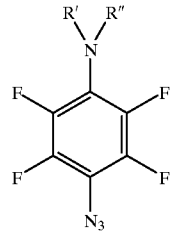

wherein R' and R" are independently hydrogen, C$_1$–C$_8$ allylic, an acyl derivative, a sulfonamide derivative, an unsubstituted benzyl, or a benzyl substituted with up to five substituents selected from the group consisting of NO$_2$, N$_3$, NH$_2$, NHR''', N(R''')$_2$, N(R''')$_3^+$, halogen, and C$_1$–C$_8$ alkyl where R''' is hydrogen, C$_1$–C$_8$ alkyl, C$_1$–C$_8$ allylic, or an unsubstituted benzyl.

2. A compound comprising the compound of claim 1 wherein said compound is 4-azidotetrafluoroaniline.

3. The compound of claim 1 wherein said compound is a sulfonamide derivative of 4-azidotetrafluoroaniline.

4. The compound of claim 3 wherein said sulfonamide derivative is 1-(4-azido-tetrafluoroaniline)-dansylsulfonamide.

5. The compound of claim 1 wherein said compound is an acyl derivative of 4-azidotetrafluoroaniline.

6. The compound of claim 5 wherein said acyl derivative is N-iodo-acetamido-4-tetrafluoroaniline.

\* \* \* \* \*